(12) United States Patent
Shoji et al.

(10) Patent No.: US 7,911,350 B2
(45) Date of Patent: Mar. 22, 2011

(54) ALCOHOL DETECTION SYSTEM

(75) Inventors: Rihito Shoji, Osaka (JP); Junichi Yukawa, Nara (JP); Fumiyasu Konno, Osaka (JP); Toshio Ishizaki, Hyogo (JP)

(73) Assignee: Panasonic Corporation, Osaka (JP)

( * ) Notice: Subject to any disclaimer, the term of this patent is extended or adjusted under 35 U.S.C. 154(b) by 409 days.

(21) Appl. No.: 12/139,538

(22) Filed: Jun. 16, 2008

(65) Prior Publication Data

US 2008/0316037 A1 Dec. 25, 2008

(30) Foreign Application Priority Data

Jun. 25, 2007 (JP) .................................. 2007-165956

(51) Int. Cl.
*G08B 23/00* (2006.01)
(52) U.S. Cl. .................... 340/576; 340/426.11; 340/5.51
(58) Field of Classification Search .................. 340/576, 340/573.1, 540, 5.1, 5.2, 5.51, 5.52, 825, 340/425.5, 426.1, 426.11, 603
See application file for complete search history.

(56) References Cited

U.S. PATENT DOCUMENTS

| | | | |
|---|---|---|---|
| 5,944,661 A | 8/1999 | Swette et al. | |
| 5,969,615 A | 10/1999 | Ivey, Jr. et al. | |
| 6,060,989 A * | 5/2000 | Gehlot | 340/576 |
| 6,229,908 B1 * | 5/2001 | Edmonds et al. | 382/124 |
| 6,748,301 B1 * | 6/2004 | Ryu | 701/1 |
| 7,736,903 B2 * | 6/2010 | Lambert et al. | 436/132 |
| 2002/0127145 A1 * | 9/2002 | Der Ghazarian et al. | 422/83 |
| 2006/0153740 A1 * | 7/2006 | Sultan et al. | 422/88 |

FOREIGN PATENT DOCUMENTS

JP  2005-224319 A  8/2005

* cited by examiner

*Primary Examiner* — Daniel Previl
(74) *Attorney, Agent, or Firm* — Panasonic Patent Center; Dhiren Odedra; Kerry Culpepper

(57) ABSTRACT

A drunk driving detection system to be incorporated in a vehicle includes a steering wheel, a film, a pair of contact detection electrodes, an alcohol sensor, and a control circuit. The steering wheel is provided with an opening in a portion to be grasped by a driver. The film is liquid-impermeable and air-permeable, and covers the first opening. The contact detection electrodes are provided on the film. The alcohol sensor is provided in a space in communication with the opening. The control circuit is connected to the contact detection electrodes and the alcohol sensor, and measures the resistance between the contact detection electrodes. When the resistance is within a predetermined range, the control circuit determines that the driver is in contact with the film and detects an alcohol drinking condition of the driver based on the output from the alcohol sensor.

20 Claims, 15 Drawing Sheets

ALCOHOL DETECTION SYSTEM

BACKGROUND

The present invention relates to an alcohol detection system to detect the level of alcohol consumed by a person. As one example, a drunk driving detection system is provided for a motor vehicle that detects mainly an alcohol drinking condition of the driver.

In recent years, a drunk driving detection system for detecting an alcohol drinking condition of a driver has been developed to reduce the number of accidents caused by drunk driving. Further, studies are made on various systems for controlling the start and operation of a motor vehicle (hereinafter referred to as "vehicle") based on the output from the drunk driving detection system.

In such a drunk driving detection system, an alcohol sensor detects a concentration of alcohol typically in exhalation. This system utilizes the proportionality between the alcohol concentration in the blood increased by alcohol-drinking and the alcohol concentration in the exhalation. Such types of systems are also used in crackdown of drunk driving. However, in detection of an alcohol drinking condition of a driver by this method, illicit acts cannot be eliminated. Such illicit acts include packing into a balloon the air exhaled by another non-drunk person, or the air exhaled when the driver drinks no alcohol, and blowing the air into the drunk driving detection system. Further, when a drunk driving detection system is installed inside of a vehicle, alcohol contained in the air exhaled by a fellow passenger or in an aromatic substance such as fragrance can cause the system to erroneously detect that the driver is drunk.

A drunk driving detection system is provided that detects an alcohol concentration in the perspiration, which is proportional to the alcohol concentration in the blood, like an alcohol concentration in the exhalation. FIG. 15 is a schematic diagram showing the structure of such a drunk driving detection system.

Sensor elements 105 for detecting alcohol are provided in parts of a steering wheel 101 and a speed change gear knob 103 which are located near the drivers seat of a vehicle and which are to be in contact with the palms of the driver. Each sensor element 105 is made of a pair of electrodes, and an alcohol-sensitive film covering the electrodes. Sensor element 105 utilizes a phenomenon that absorption of an alcohol component to the alcohol-sensitive film changes the resistance between the electrodes. Thus, when the perspiration vapor generated from the palms reaches sensor element 105, the sensor element can detect an alcohol concentration in the perspiration. The output signal from sensor element 105 is transmitted to alcohol concentration measurement unit 107, where an alcohol concentration is obtained. The alcohol concentration output obtained in alcohol concentration measurement unit 107 is transmitted to drunk driving determiner 109, where an alcohol drinking condition of the driver is determined. The determination result is transmitted to post-stage processor 111. If the driver is in a drunk condition, post-stage processing, such as inhibition, warning, prevention, and control of drunk driving, is performed. Specifically, post-stage processor 111 locks the vehicle to inhibit the start thereof, or reduces the speed while the vehicle is running.

In this manner, installation of sensor elements 105 in a steering wheel and a speed change gear knob 103 to be operated by a driver allows the detection of the alcohol concentration in the perspiration of the driver. Thus, the possibility of illicit acts or erroneous detection can be reduced in comparison with the alcohol detection using the exhalation.

Further, after piezoelectric elements or the like disposed in proximity to sensor elements 105 determine whether or not the hand of a driver has touched steering wheel 101, the drunk driving detection system is activated. Thus, the detection accuracy is improved.

Such a drunk driving detection system can detect an alcohol drinking condition of the driver with high accuracy. However, disposition of the piezoelectric elements or the like in proximity to sensor elements 105 causes the following problems. For example, when the driver places the palm on steering wheel 101 so that the palm touches the piezoelectric element but does not touch sensor element 105, the alcohol concentration in the perspiration from the palm is not detected although the drunk driving detection system is activated. As a result, illicit acts for evading detection of an alcohol drinking condition can be performed.

SUMMARY

A drunk driving detection system of the present invention is incorporated in a motor vehicle, and includes a steering wheel, a film, a pair of contact detection electrodes, an alcohol sensor, and a control circuit. The steering wheel provided with an opening in a portion thereof to be grasped by a driver. The film is liquid-impermeable and air-permeable, and covers the opening. The contact detection electrodes are provided on the surface of the film. The alcohol sensor is provided in a space in communication with the opening. The control circuit is connected to the contact detection electrodes and the alcohol sensor, and measures the resistance between the contact detection electrodes. When the resistance is within a predetermined range, the control circuit determines that the driver is in contact with the film and detects an alcohol drinking condition of the driver based on the output from the alcohol sensor.

DETAILED DESCRIPTION

First Exemplary Embodiment

Figure 1:
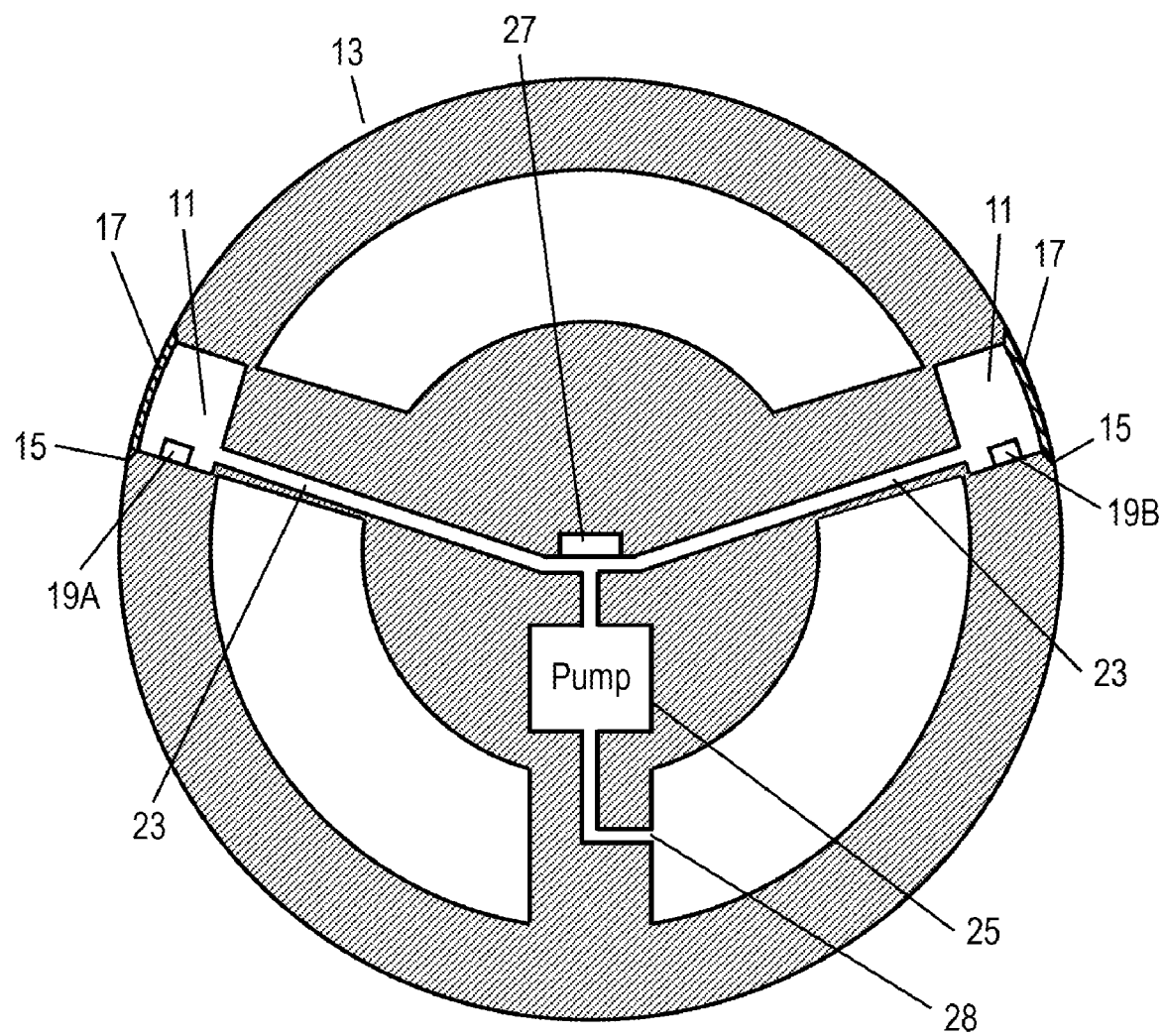
FIG. 1 is a schematic sectional view of a drunk driving detection system in accordance with a first exemplary embodiment of the present invention.
Figure 2A:
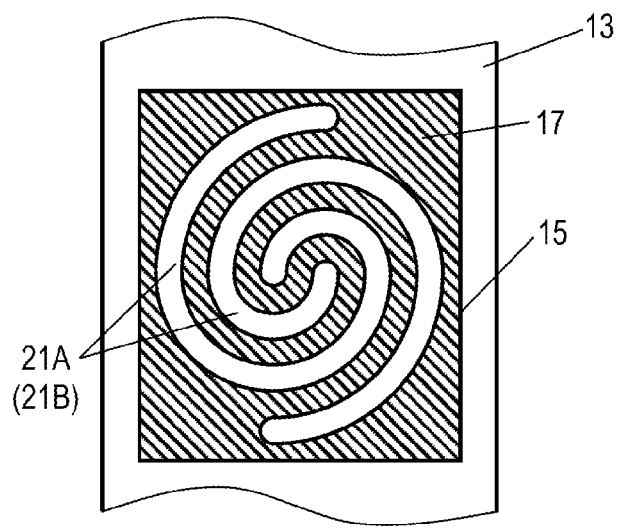
FIGS. 2A through 2C are plan views showing configurations of pairs of contact detection electrodes in the drunk driving detection system of FIG. 1.
Figure 2B:
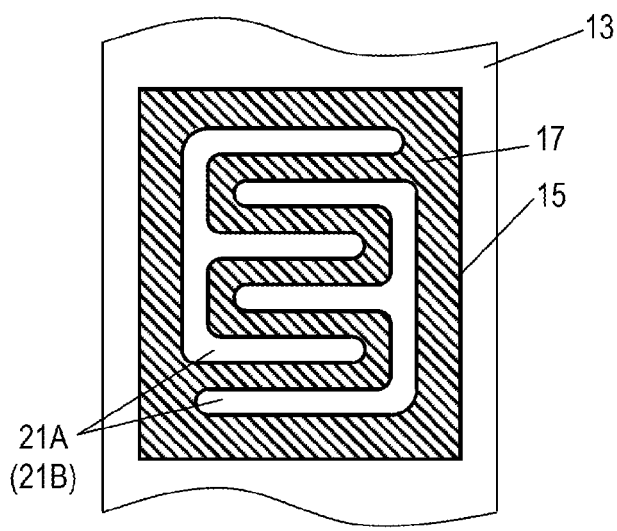
Figure 2C:
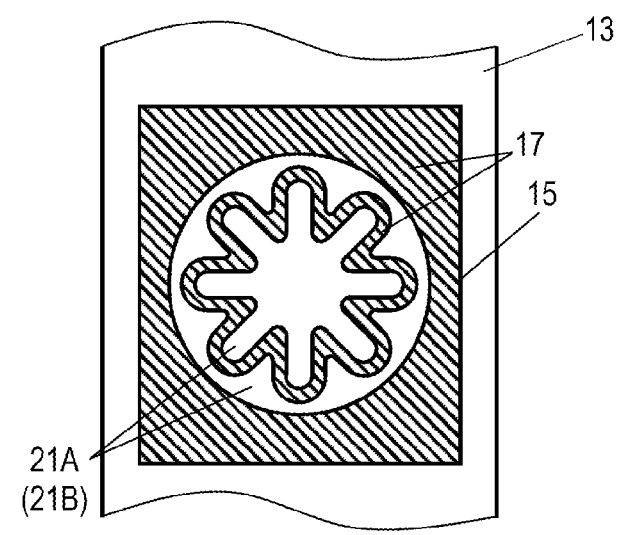
Figure 3:
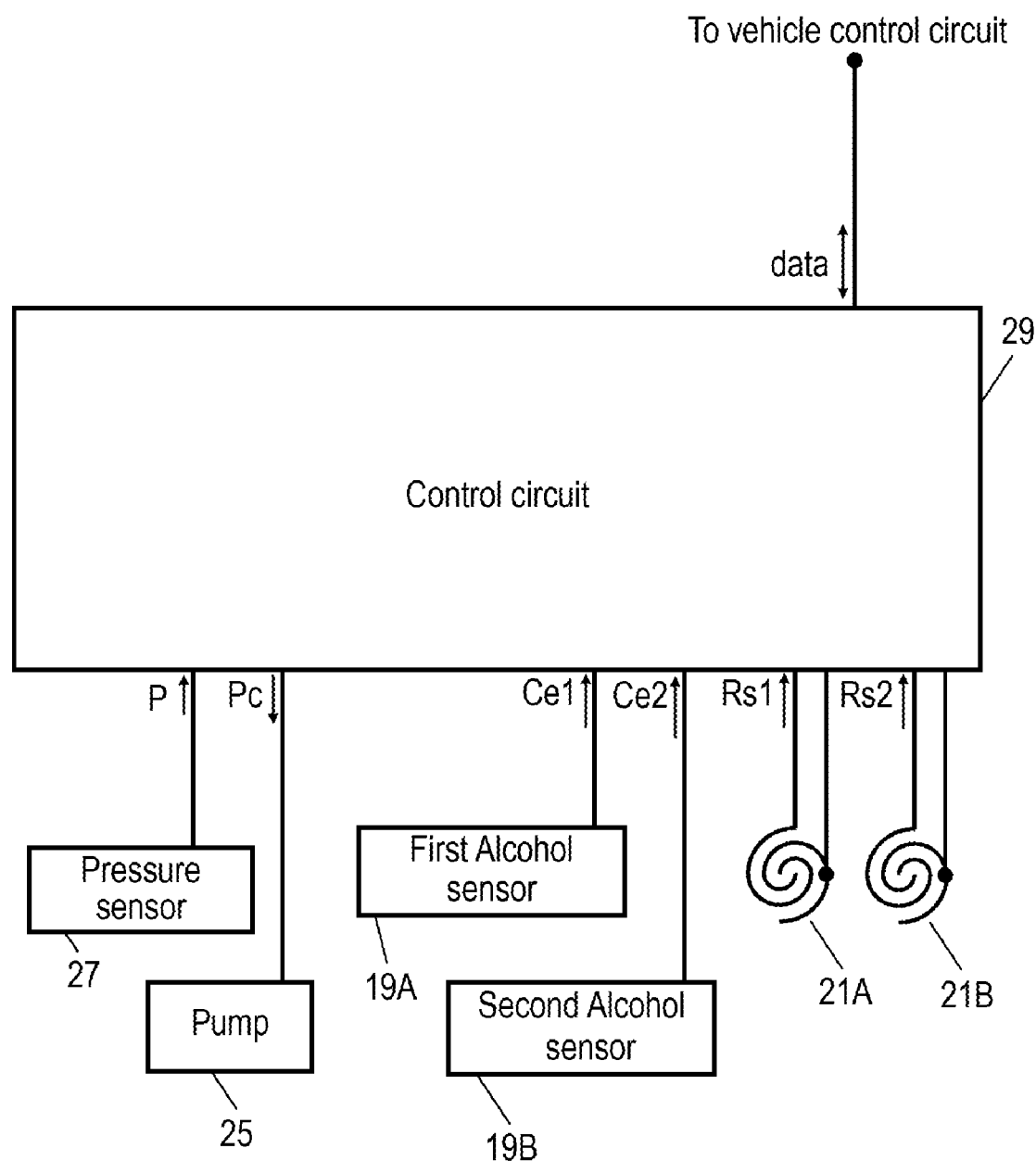
FIG. 3 is a block circuit diagram of the drunk driving detection system of FIG. 1.
Figure 4:
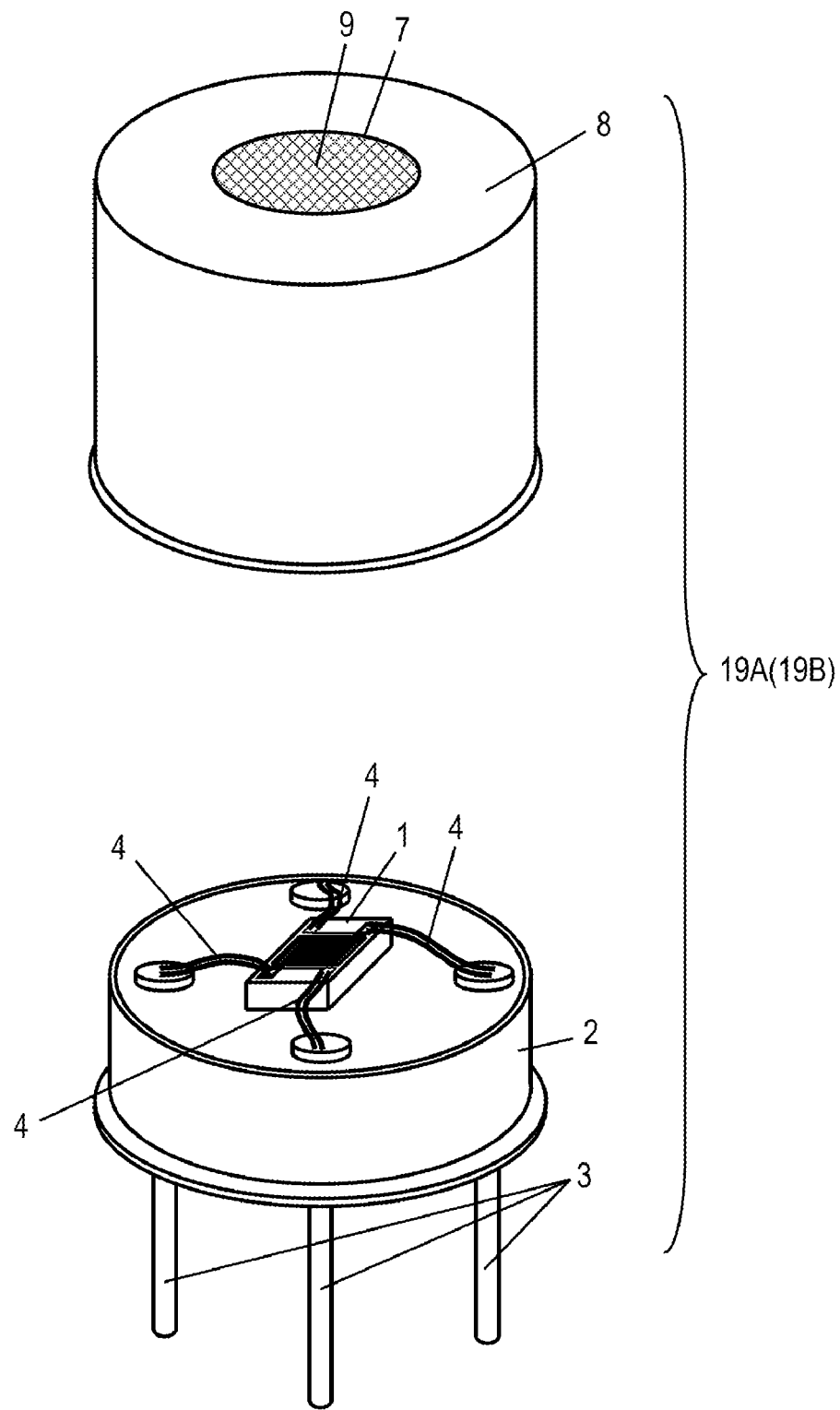
FIG. 4 is an exploded perspective view of an alcohol sensor in the drunk driving detection system of FIG. 1.
Figure 5:
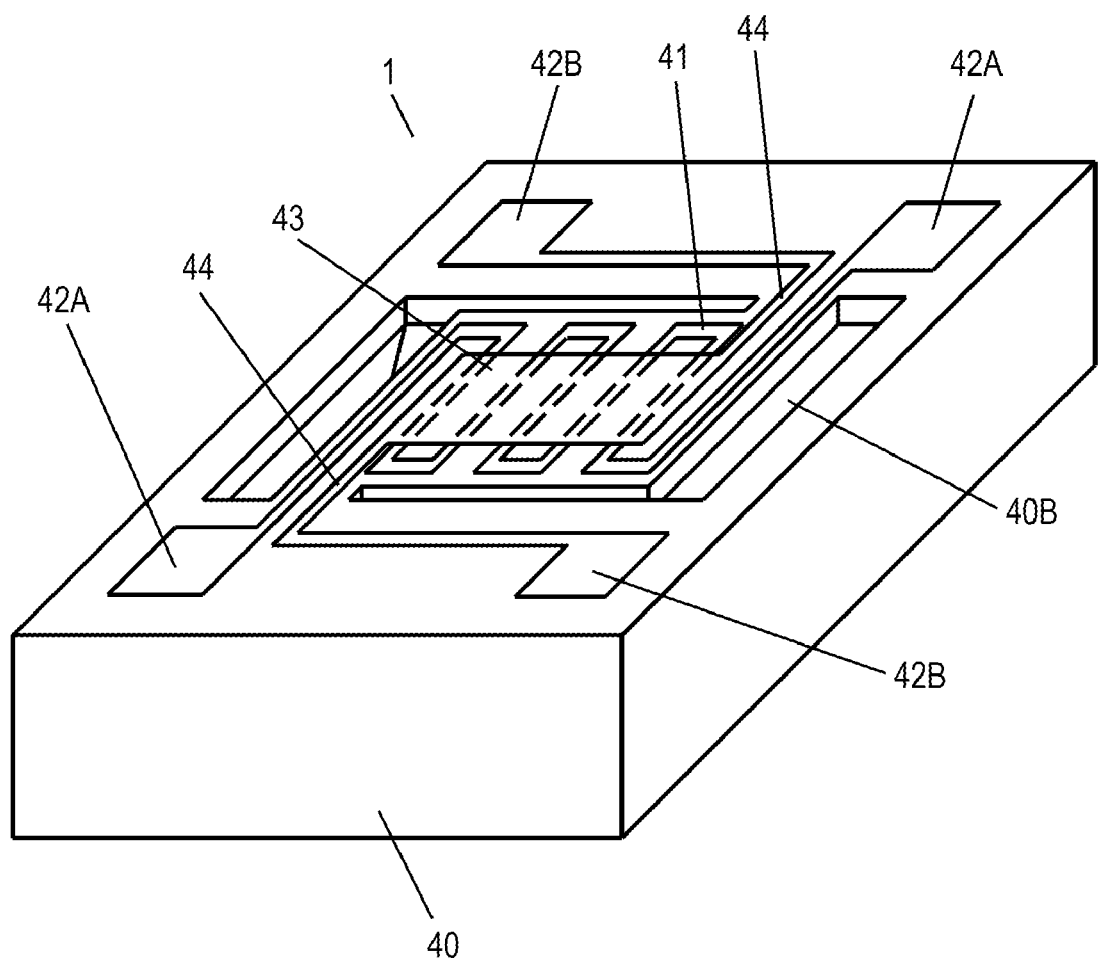
FIG. 5 is a perspective view of an alcohol detecting element in the alcohol sensor of FIG. 4.
Figure 6:
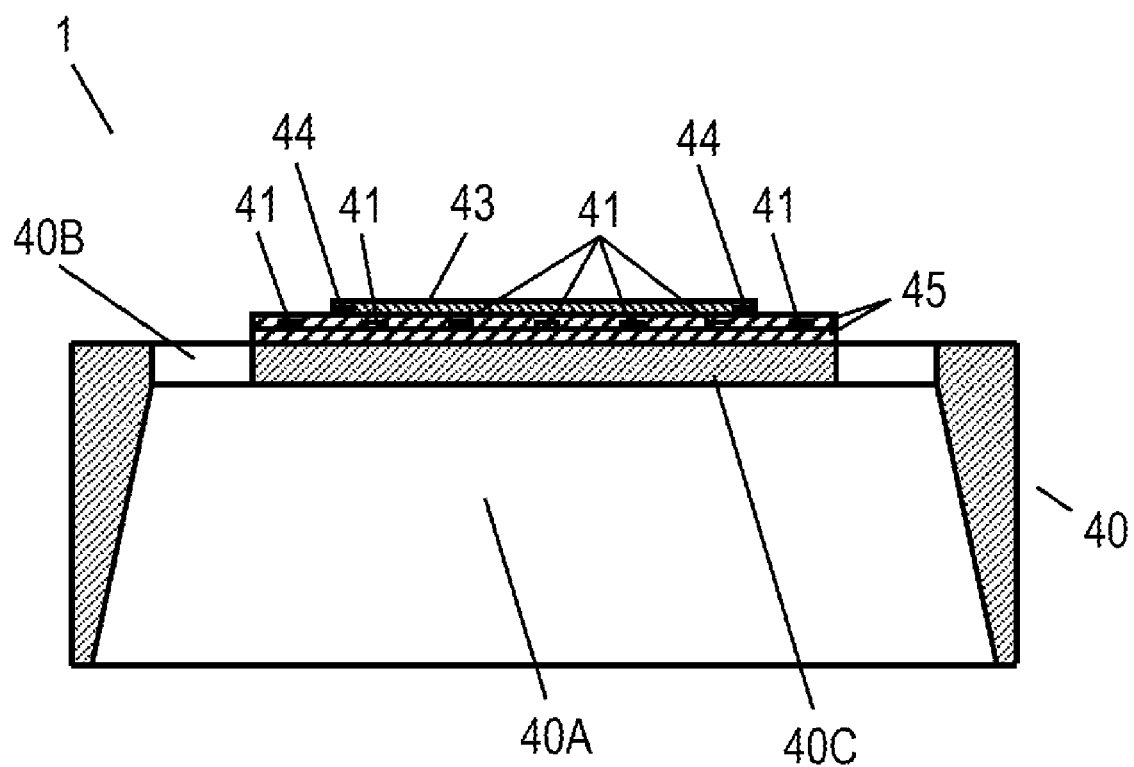
FIG. 6 is a sectional view of the alcohol detecting element in the alcohol sensor of FIG. 4.
Figure 7:
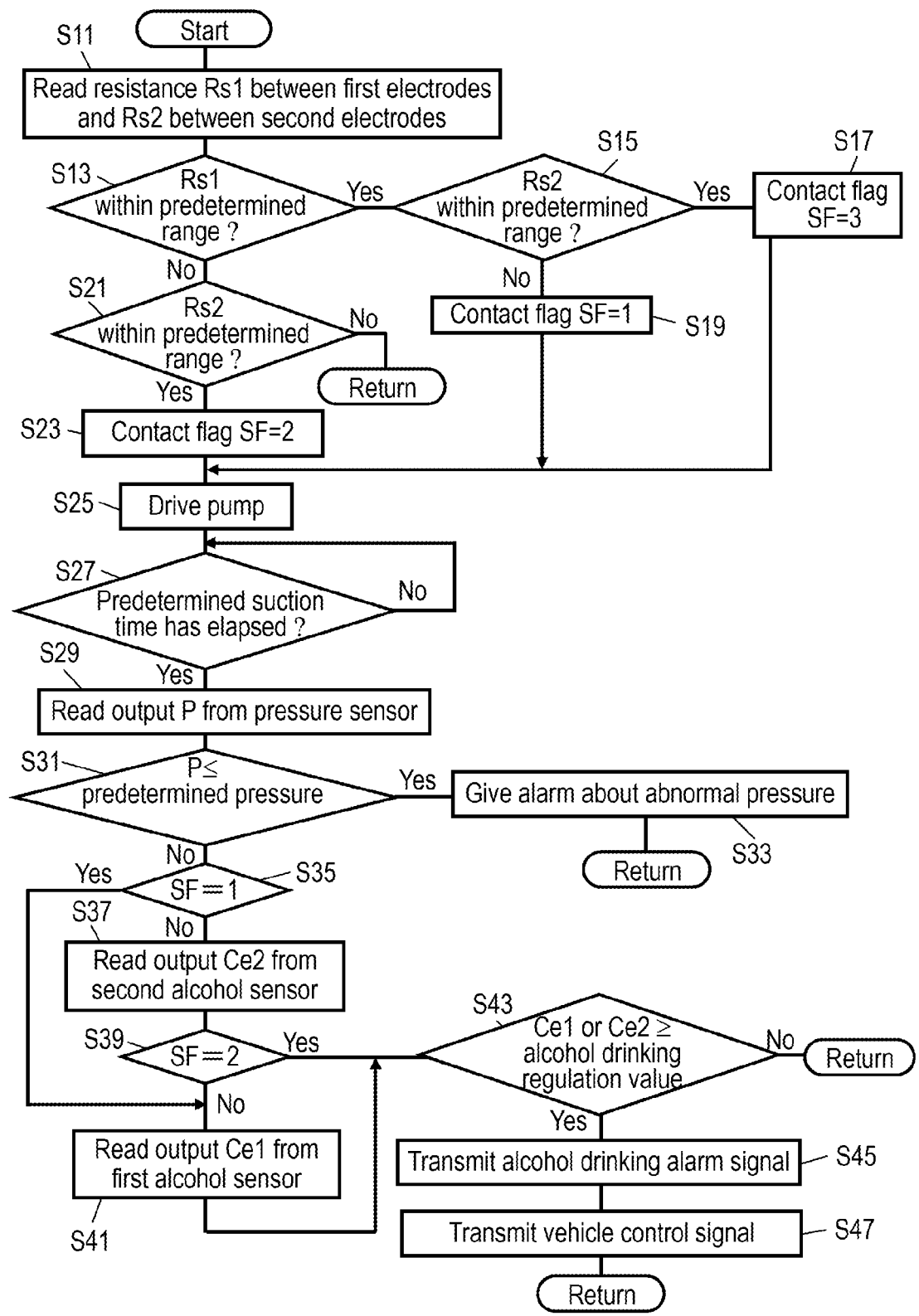
FIG. 7 is a flowchart showing the operation of the drunk driving detection system of FIG. 1.
Figure 8:
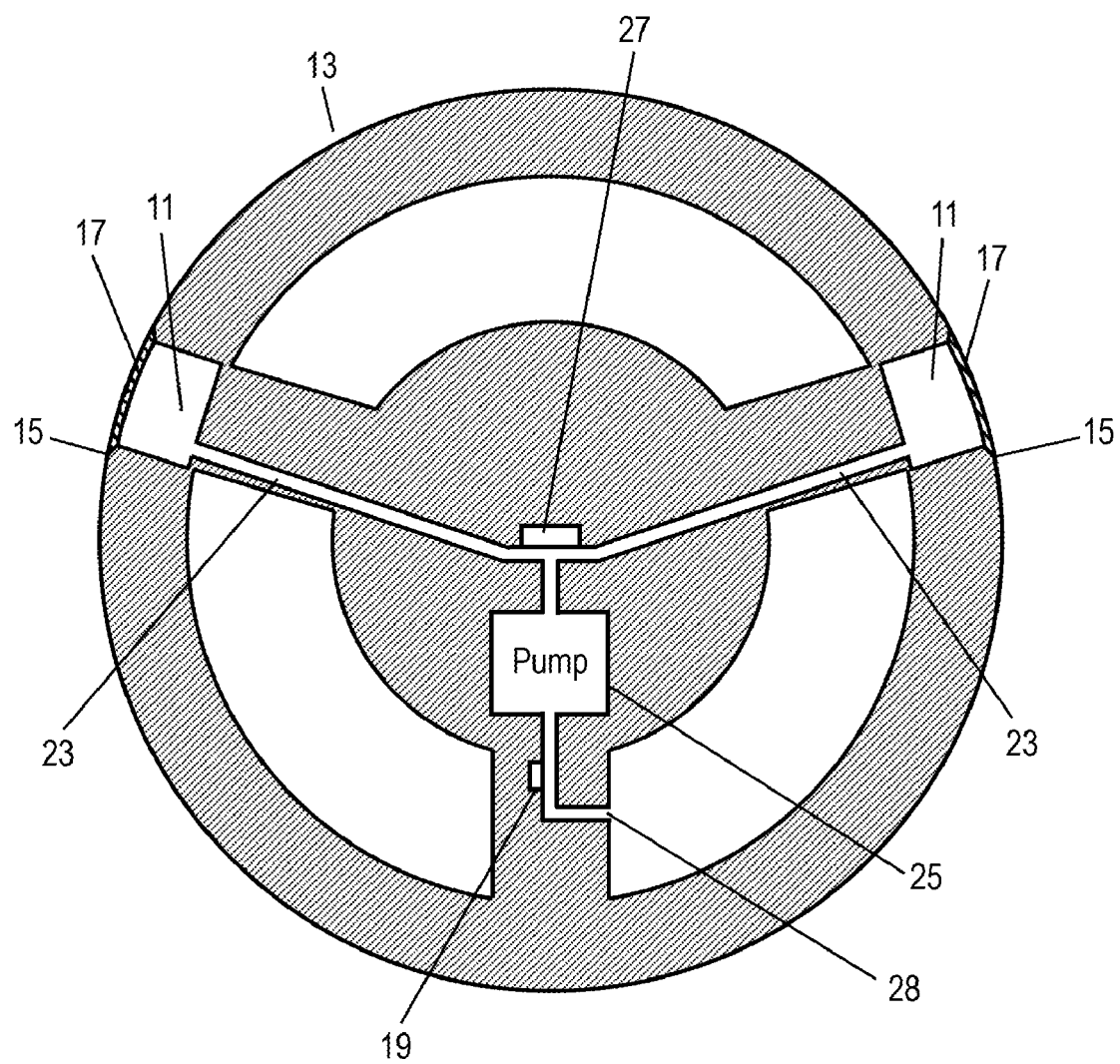
FIGS. 8 through 10 are schematic sectional views of other structures of the drunk driving detection system in accordance with the first exemplary embodiment of the present invention.
Figure 9:
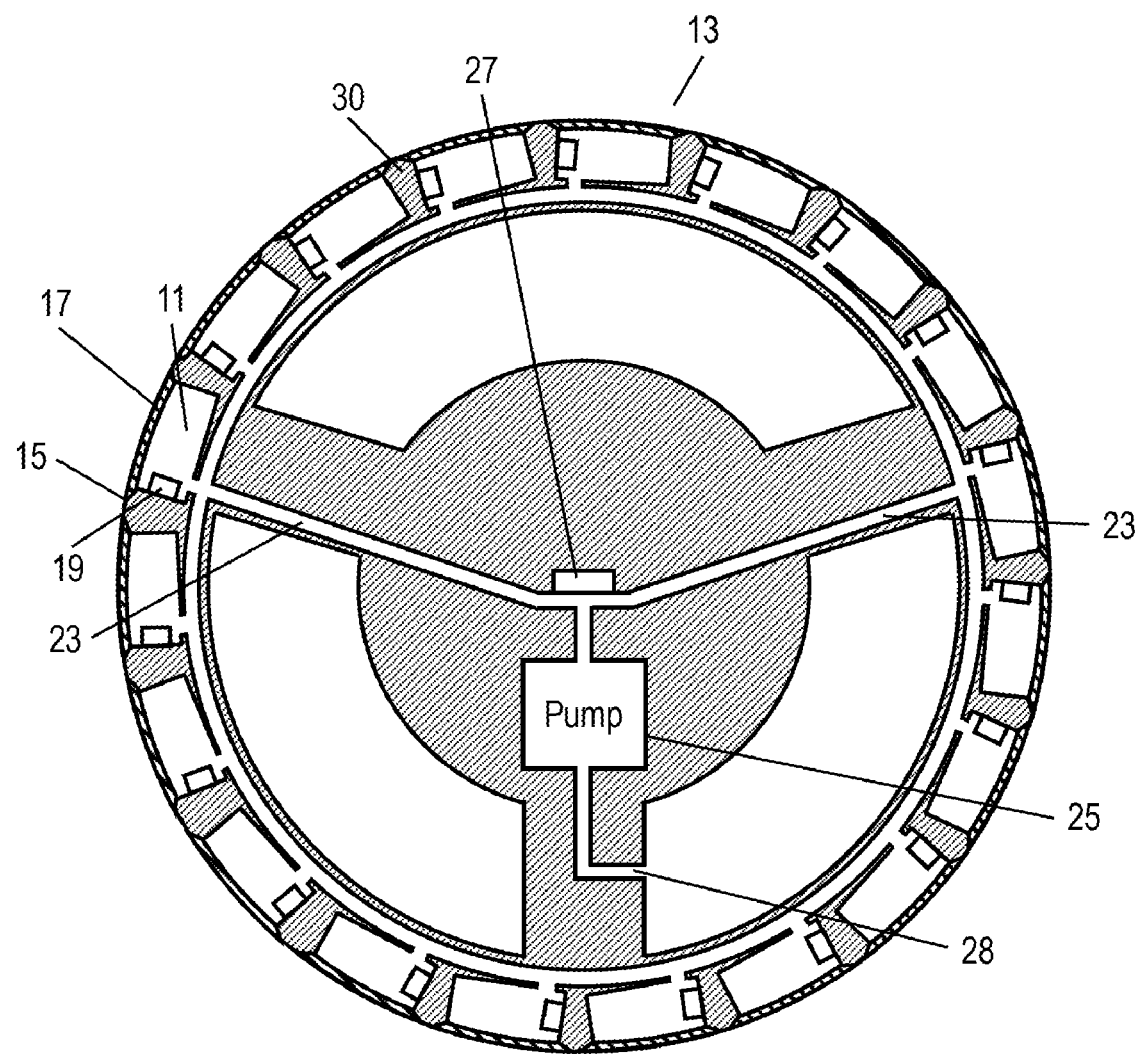
Figure 10:
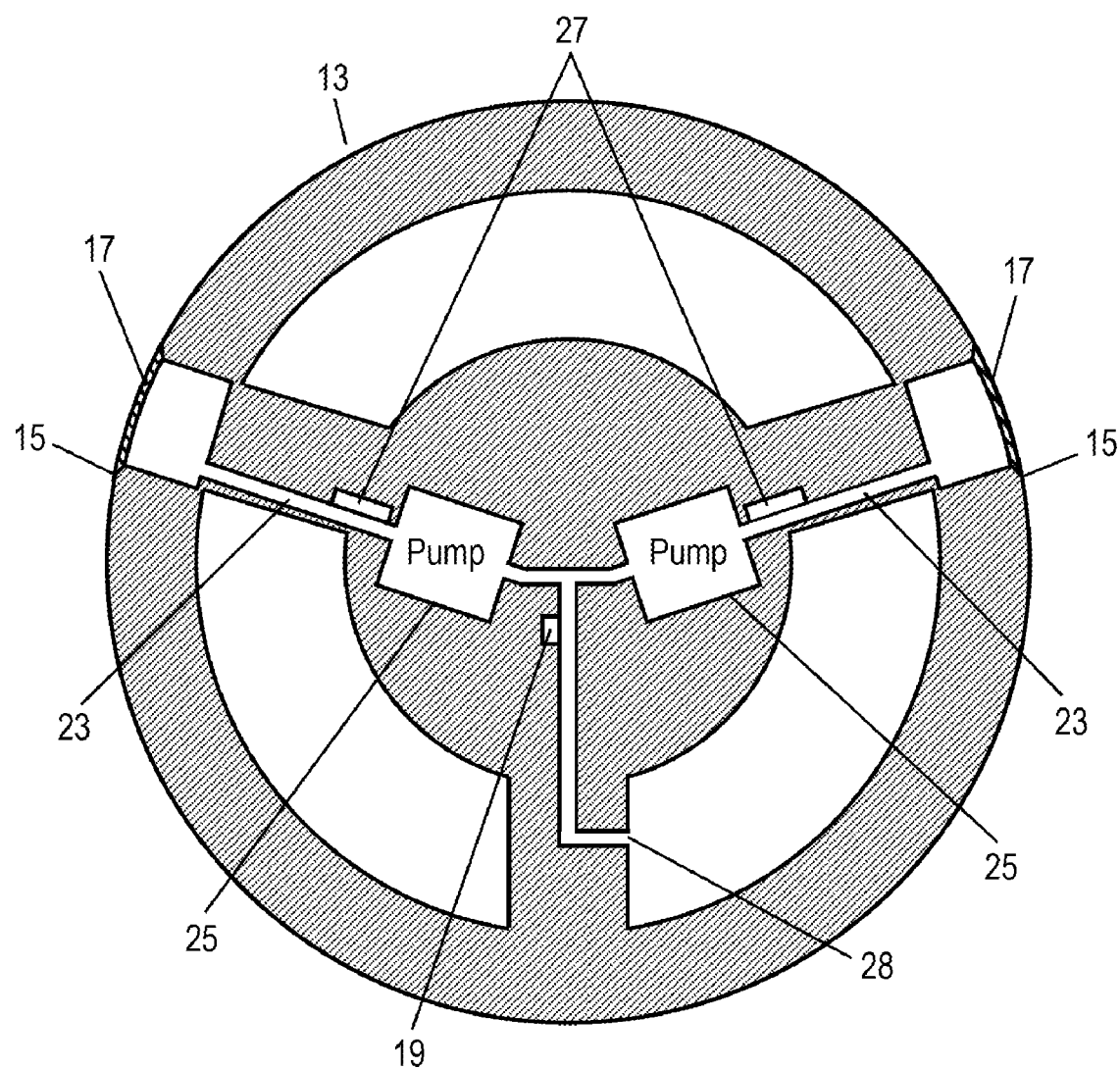

FIG. 1 is a schematic sectional view of a drunk driving detection system in accordance with a first exemplary embodiment of the present invention. FIGS. 2A through 2C are plan views showing configurations of pairs of contact detection electrodes in the drunk driving detection system. FIG. 3 is a block circuit diagram of the drunk driving detection system of FIG. 1. FIG. 4, FIG. 5, and FIG. 6 are an exploded perspective view, a perspective view, and a sectional view, respectively, of an alcohol sensor in the drunk driving detection system. FIG. 7 is a flowchart showing the operation of the drunk driving detection system of FIG. 1. FIG. 8, FIG. 9, and FIG. 10 are schematic sectional views of other structures of the drunk driving detection system in accordance with this exemplary embodiment.

This drunk driving detection system is to be incorporated into a motor vehicle. The drunk driving detection system includes steering wheel 13, films 17, a pair of first contact detection electrodes 21A, first alcohol sensor 19A, a pair of second contact detection electrodes 21B, second alcohol sensor 19B, and control circuit 29. Steering wheel 13 is provided with openings 15 in portions thereof to be grasped by a driver. Films 17 cover openings 15. Contact detection electrodes 21A and 21B are provided on the surfaces of respective films 17. Each of alcohol sensors 19A and 19B is provided in a space inside of steering wheel 13 in communication with corresponding openings 15. With reference to FIG. 1, alcohol sensors 19A and 19B are provided in proximity to openings 15. Control circuit 29 is connected to contact detection electrodes 21A and 21B, and alcohol sensors 19A and 19B as shown in FIG. 3. Control circuit 29 measures the resistance between contact detection electrodes 21A and the resistance between contact detection electrodes 21B. When at least one of the resistance values is within a predetermined range, the control circuit determines that the driver is in contact with at least one of films 17 and detects an alcohol drinking condition of the driver based on the output from at least one of alcohol sensors 19A and 19B.

Alcohol detection parts 11 are incorporated within steering wheel 13. Alcohol detection parts 11 are disposed in two positions in steering wheel 13. The detailed structure of each alcohol detection part 11 is as follows. Alcohol detection part 11 is formed in a space made by hollowing a part of steering wheel 13. Along the outer periphery of steering wheel 13, opening 15 for capturing the perspiration vapor from a palm is provided. Film 17 is provided so as to cover the entire part of opening 15. Behind openings 15, i.e. inside of steering wheel 13, alcohol sensors 19A and 19B are provided.

Each film 17 works to pass only the perspiration vapor and no liquid perspiration from the palm. In other words, film 17 is liquid-impermeable and air-permeable. Alcohol sensors 19A and 19B provided behind openings 15 detect a concentration of alcohol that is contained in the perspiration vapor introduced from openings 15 through films 17.

As described above, film 17 is liquid-impermeable. This property can reduce failures such that wet alcohol sensors 19A and 19B cannot detect an alcohol concentration. As film 17 having such property, an oriented porous fluorocarbon resin can be used. Film 17 is extremely thinner than steering wheel 13; however, in order to simplify understanding, FIG. 1 shows the thickness of films 17 larger than the actual thickness. Beam-shaped members for supporting the entire part of films 17 are also disposed in contact with films 17. However, the beam-shaped members are omitted in FIG. 1.

Provided on the surfaces of films 17 are pairs of contact detection electrodes 21A and 21B having either one of configurations shown in FIG. 2A through 2C. Contact detection electrodes 21A and 21B are provided in order to detect whether or not openings 15 (films 17) are in contact with the palms. Hereinafter, a description is provided of contact detection electrodes 21A as an example.

Control circuit 29 of FIG. 3 determines that a palm is in contact with film 17 by detecting the resistance between contact detection electrodes 21A, i.e. the resistance of the skin of the palm. In this manner, control circuit 29 detects that the palm is in contact with film 17 provided over opening 15 by contact detection electrodes 21A. Further, in this condition, control circuit 29 detects an alcohol concentration in the perspiration of the palm by alcohol sensors 19A and 19B. Thus, illicit acts can be reduced.

Film 17 is made of a resin and thus has electrical insulating property. Therefore, contact detection electrodes 21A are directly fixed onto the surface of film 17 so that they are out of contact with each other. When film 17 has electrical conductivity, contact detection electrodes 21A may be fixed to film 17 with an insulating layer disposed therebetween.

Next, a description is provided of the detailed structure of contact detection electrodes 21A, with reference to FIGS. 2A through 2C. These drawings are plan views as film 17 is seen from the outside thereof.

Contact detection electrodes 21A have a configuration in which they are intricate into each other. For example, FIG. 2A shows a spiral configuration. In this configuration, it is extremely difficult to perform an illicit act of covering only film 17 with a moisture-impermeable film or the like while intentionally avoiding covering contact detection electrodes 21A so that an alcohol drinking condition is not detected. If the entire part of opening 15 is covered with a moisture-impermeable film or the like, the skin resistance is always undetectable by contact detection electrodes 21A. Thus, control circuit 29 can determine an illicit act.

Other than the spiral configuration of FIG. 2A, contact detection electrodes 21A can be configured in a comb-shaped configuration of FIG. 2B or a star-shaped configuration of FIG. 2C in which the two electrodes are intricate into each other. Any configuration may be used as long as the configuration hinders covering not contact detection electrodes 21A but only film 17 with a moisture-impermeable film or the like.

Next, a description is provided of the detailed structure of alcohol sensors 19A and 19B, with reference to FIGS. 4 through 6. A description is provided of alcohol sensor 19A as an example.

FIG. 4 is an exploded perspective view of alcohol sensor 19A. Alcohol detecting element 1 is fixed onto base 2. Base 2 has four pins 3 penetrating through base 2. The top face of each pin 3 is connected to alcohol detecting element 1 by two gold wires 4. The use of each two wires 4 allows continuous use of alcohol sensor 19A even if one of wires 4 is broken, because the other of wires 4 is still connected. Thus, the reliability is improved. Cap 8 including hole 7 is fitted over base 2. Base 2 and cap 8 are fixed to each other by resistance welding. Over hole 7, stainless-steel net 9 is fixed with cap 8. Thus, perspiration vapor reaches alcohol detecting element 1 through net 9 disposed over hole 7.

Next, a description is provided of the detailed structure of alcohol detecting element 1. FIG. 5 is a perspective view of alcohol detecting element 1. FIG. 6 is a sectional view thereof. Alcohol detecting element 1 includes micro heater 41 having a meander pattern on the surface of silicon pedestal 40, and semiconductor device 43 of a thin film formed on micro heater 41. Micro heater 41 is formed of a platinum thin film, and thus is capable of enduring high temperatures. Semiconductor device 43 is formed of a thin-film of tin oxide. Both ends of micro heater 41 are connected to lands 42A. Further, semiconductor device 43 is coupled to lands 42B via extraction electrodes 44. Lands 42A and 42B are connected to wires 4 shown in FIG. 4.

As shown in FIG. 6, micro heater 41 and semiconductor device 43 are formed on the surface (the top face in FIG. 6) opposite to the surface that has recess 40A formed by micromachining. The thickness of thin plate part 40C formed by recess 40A is approximately 10 µm, for example. In order to prevent the short circuit between pedestal 40 made of silicon, i.e. a semiconductor, and micro heater 41, insulating layer 45 is formed between thin plate part 40C and micro heater 41. Thus, micro heater 41 is formed on the top face of insulating layer 45. Extraction electrodes 44 and semiconductor device 43 are further formed on the top face of micro heater 41 via insulating layer 45. In this manner, micro heater 41 is electrically insulated from pedestal 40 and semiconductor device 43.

Providing micro heater 41 on thin plate part 40C in this manner can extremely reduce the heat capacity. Further, providing gap 40B to minimize the portion connected to pedestal 40 can inhibit heat conduction to pedestal 40. Thermal coupling between micro heater 41 and semiconductor device 43 via insulating layer 45 facilitates heat conduction to semiconductor device 43. With these structures, the heat capacity of micro heater 41 is extremely reduced, and semiconductor device 43 can be heated to a sufficient temperature even at minute electric current. Each of micro heater 41, semiconductor device 43, extraction electrodes 44, and insulating layers 45 has a thickness of approximately several micrometers. However, FIG. 6 shows the dimensions thereof exaggeratingly larger than the actual dimensions to simplify understanding.

Semiconductor device 43 detects an alcohol concentration in a condition heated by micro heater 41 to a temperature appropriate for alcohol detection. This temperature depends on the material of semiconductor device 43, and is approximately several hundred degrees Celsius. However, large power is consumed to keep semiconductor device 43 at such a high temperature. For this reason, semiconductor device 43 is located immediately above micro heater 41. This structure can extremely reduce the heat capacity of alcohol sensor 19A. Thus, the temperature of semiconductor device 43 can be risen to a preset temperature at a low current, e.g. approximately several milliamperes, within a short time period, e.g. 0.1 second or shorter.

When an alcohol component is brought into contact with semiconductor device 43 heated by micro heater 41, with oxidation of the alcohol component, semiconductor device 43 is reduced. As a result, the resistance of semiconductor device 43 changes. In a case that semiconductor device 43 is made of a tin oxide, the resistance decreases. Control circuit 29 measures changes in the resistance between lands 42B to calculate the alcohol concentration.

Meanwhile, the alcohol concentration need not be detected at all times. The alcohol concentration may be detected only when it is detected that a palm has made contact with film 17 by contact detection electrodes 21A or contact detection electrodes 21B after the out-of-contact state. For this reason, the alcohol concentration is detected using pulse current passing through micro heater 41. For example, only a current of 7 mA supplied for 0.2 second can complete the temperature rise, thus allowing detection of an alcohol concentration. The use of such current can reduce the power consumption in alcohol sensors 19A and 19B. The accuracy in detecting alcohol concentrations can be improved by repeating the detection using pulsed current at a plurality of times and providing an average output value. At this time, control circuit 29 operates only alcohol sensor 19A when the contact of a palm is detected in contact detection electrodes 21A, and operates only alcohol sensor 19B when the contact of a palm is detected in contact detection electrodes 21B. When the contact of palms is detected in both contact detection electrodes 21A and 21B, control circuit 29 activates both alcohol sensors 19A and 19B. These operations allow at least one of alcohol sensors 19A and 19B to securely be operated with respect to a subject of alcohol detection only, and thus are preferable.

The pulse current may be supplied also before the detection of an alcohol concentration by utilizing the fast temperature rise characteristics of alcohol sensors 19A and 19B. With this operation, impurities, such as moisture, absorbing to the surface of semiconductor device 43 are removed by heating. This operation allows detection of an alcohol concentration with the surface of semiconductor device 43 in a clean condition. Thus, detection accuracy can further be improved. All the pulse current supplied to alcohol sensors 19A and 19B is controlled by control circuit 29.

Each of alcohol sensors 19A and 19B may include a plurality of semiconductor devices 43. Micro heater 41 is fabricated extremely small by micromachining technology. Using this technology, a plurality of micro heaters 41 can collectively be fabricated in one alcohol sensor and semiconductor device 43 is formed on each micro heater. A plurality of semiconductor devices 43 provided in this manner can extend the life of alcohol sensors 19A and 19B for the following reason. Even if a failure is caused by deterioration, breakage of wires or the like in one of semiconductor devices 43, the other normal ones of semiconductor devices 43 can be used in place of the failed one.

Further, control circuit 29 may sequentially switch the plurality of semiconductor devices 43 every time an alcohol concentration is detected. In this case, the deterioration degrees of the plurality of semiconductor devices 43 are averaged and the frequency of use per semiconductor device is reduced. This structure extends the life of alcohol sensors 19A and 19B. This structure can also inhibit variations in the output from respective semiconductor devices 43.

It is preferable that the intake side of pump 25 is coupled to alcohol detection parts 11 provided with openings 15, via suction pipes 23 each incorporated in steering wheel 13. In this structure, pump 25 sucks air containing perspiration vapor through films 17, and exhausts the air from exhaust port 28. For example, a small pump, e.g. a piezoelectric pump, can be used as pump 25, which can be installed in steering wheel 13.

When control circuit 29 detects that a palm is in contact with film 17 by contact detection electrode pair 21A or contact detection electrode 21B, control circuit 29 operates pump 25. This operation causes the perspiration vapor from the palm to be evaporated and positively introduced to alcohol sensors 19A and 19B. Thus, alcohol sensors 19A and 19B can detect alcohol concentrations in the perspiration vapor at high speeds. It is preferable that exhaust port 28 is provided at a distance from openings 15 so that the alcohol vapor contained in the exhaust air from exhaust port 28 does not affect the detection.

In FIG. 1, pump 25 is provided inside of steering wheel 13. However, pump 25 may be provided outside of steering wheel 13 and connected to suction pipes 23 by tubes or the like.

It is preferable that pressure sensor 27 is provided between openings 15 and pump 25. With pressure sensor 27, control circuit 29 can detect that film 17 is blocked, when the pressure output from pressure sensor 27 during operation of pump 25 is equal to or lower than a predetermined pressure. Then, control circuit 29 determines that alcohol concentrations cannot be measured properly at this time.

Next, a description is provided of the circuit structure of the drunk driving detection system, with reference to FIG. 3. Alcohol sensors 19A and 19B, contact detection electrodes 21A and 21B, pump 25, and pressure sensor 27 are connected to control circuit 29. Control circuit 29 is made of microcomputers and peripheral circuits, and controls the entire part of the drunk driving detection system. Fed into control circuit 29 are resistance Rs1 between contact detection electrodes 21A, resistance Rs2 between contact detection electrodes 21B, output Ce1 from alcohol sensor 19A, and output Ce2 from alcohol sensor 19B, and output P from pressure sensor 27. The operation of pump 25 is controlled by pump driving signal Pc (including driving power of pump 25) from control circuit 29.

Further, control circuit 29 communicates with the vehicle control circuit to exchange various kinds of information, such as detection results of alcohol drinking conditions, and unlocking and locking conditions. The communicated data is fed into and supplied from control circuit 29 as data signal data.

Next, a description is provided of the operation of the drunk driving detection system, with reference to the flowchart of FIG. 7. This flowchart shows a subroutine to be executed every predetermined period of time (e.g. every one minute) from the main routine (not shown).

When the main routine executes the subroutine of FIG. 7, control circuit 29 reads resistance Rs1 between contact detection electrodes 21A, and resistance Rs2 between contact detection electrodes 21B at first (S11). Next, control circuit 29 determines whether or not resistance Rs1 is within a predetermined range (S13). The predetermined range of resistance Rs1 is a range within which skin resistance exists. In this exemplary embodiment, the range is set from 2 kΩ to 5 kΩ inclusive. However, this range varies with the size and shape of contact detection electrodes 21A and the distance between the two electrodes. Thus, the range of the skin resistance corresponding to contact detection electrodes 21A is predetermined and stored in a memory of control circuit 29.

When resistance Rs1 is within the predetermined range (Yes in S13), control circuit 29 determines that the left hand is in contact with contact detection electrodes 21A. Next, control circuit 29 determines whether or not the right hand is also in contact with contact detection electrodes 21B. Specifically, control circuit 29 determines whether or not resistance Rs2 between contact detection electrodes 21B is within a predetermined range (S15). The predetermined range of resistance Rs2 is equal to that of resistance Rs1.

When resistance Rs2 is within the predetermined range (Yes in S15), control circuit 29 determines that the right hand is in contact with contact detection electrode pair 21B. In other words, control circuit 29 determines that the left and right hands are in contact with contact detection electrodes 21A and contact detection electrodes 21B, respectively, at the same time. Then, in order to indicate that the left and right hands are in contact with contact detection electrodes 21A and 21B, respectively, control circuit 29 substitutes "3" for contact flag SF (S17). Contact flag SF is a memory built in control circuit 29 and a flag that indicates the following conditions. When SF is "1", the left hand is in contact with the contact detection electrode pair. When SF is "2", the right hand is in contact with the contact detection electrode pair. When SF is "3", both hands are in contact with the contact detection electrode pairs. After S17, control is jumped to S25 to be described later.

On the other hand, when resistance Rs2 is not within the predetermined range (No in S15), control circuit 29 determines that the right hand is not in contact with contact detection electrodes 21B and only the left hand is in contact. Therefore, "1" is substituted for contact flag SF (S19), and control is jumped to S25 to be described later.

Again with reference to S13, when resistance Rs1 is not within the predetermined range (No in S13), control circuit 29 determines that the left hand is not in contact with contact detection electrodes 21A and then determines whether or not the right hand is in contact. Specifically, similar to S15, control circuit 29 determines whether or not resistance Rs2 between contact detection electrodes 21B is within the predetermined range (S21). When resistance Rs2 is not within the predetermined range (No in S21), control circuit 29 determines that the left and right hands are out of contact with contact detection electrodes 21A and contact detection electrodes 21B, respectively. The operation and case assumed in this condition are as follows. The driver is sharply turning steering wheel 13, or operating components other than steering wheel 13, such as a shift lever. When the left and right hands are out of contact with contact detection electrodes 21A and contact detection electrodes 21B, respectively, in this manner, an alcohol drinking condition cannot be determined. Thus, the subroutine of FIG. 7 is terminated and control is returned to the main routine.

On the other hand, when resistance Rs2 is within the predetermined range (Yes in S21), control circuit 29 determines that only the right hand is in contact with contact detection electrodes 21B. Then, "2" is substituted for contact flag SF (S23).

Next, control circuit 29 drives pump 25 (S25) and pump 25 sucks the air in the vicinity of openings 15. The driving power of pump 25 is supplied via control circuit 29. Thereafter, control circuit 29 determines whether or not a predetermined period of suction time has elapsed (S27). The predetermined period of suction time is a period during which pump 25 is driven to replace all the air in two alcohol detection parts 11. When the predetermined period of suction time has not elapsed (No in S27), control is returned to S27 and control circuit 29 waits for the lapse of the predetermined period of suction time. When the predetermined period of suction time has elapsed (Yes in S27), control circuit 29 reads the output (pressure output P) from pressure sensor 27 (S29). Thereafter, control circuit 29 determines whether or not pressure output P is equal to or lower than a predetermined pressure (S31). The predetermined pressure is set at an absolute pressure of 0.051 MPa, for example. If openings 15 are illicitly blocked so that alcohol detection can be evaded, pressure output P from pressure sensor 27 disposed between openings 15 and pump 25 is reduced to a value equal to or lower than the predetermined pressure. Thus, monitoring pressure output P allows determination of illicit acts.

When pressure output P is equal to or lower than the predetermined pressure (Yes in S31), it is possible that illicit acts, such as blocking openings 15, are performed. Thus, abnormality in pressure is warned by an alarm (S33), and the subroutine of FIG. 7 is terminated.

On the other hand, when pressure output P is higher than the predetermined pressure (No in S31), control circuit 29 determines that the perspiration vapor in the vicinity of the palm has normally been introduced into alcohol detection part 11. Next, control circuit 29 determines whether or not contact flag SF is "1" (S35). When SF is "1" (Yes in S35), only the left hand is in contact with contact detection electrodes 21A and thus control is jumped to S41 to be described later. On the other hand, when SF is not "1" (No in S35), at least the right hand is in contact with contact detection electrodes 21B and thus control circuit 29 reads output Ce2 from alcohol sensor 19B (S37). Thereafter, control circuit 29 determines whether or not contact flag SF is "2", in order to determine whether or not the left and right hands are in contact with contact detection electrodes 21A and contact detection electrodes 21B, respectively (S39).

When SF is "2" (Yes in S39), only the right hand is in contact with contact detection electrodes 21B and thus control is jumped to S43 to be described later. On the other hand, when SF is not "2" (No in S39), SF is "3" and the left and right hands are in contact with contact detection electrodes 21A and contact detection electrodes 21B, respectively. Output Ce2 from alcohol sensor 19B has already been read in S37, and then output Ce1 from alcohol sensor 19A is read (S41). With these operations, when only the left hand is in contact with the contact detection electrode pair, i.e. when SF is "1", control circuit 29 reads output Ce1 from alcohol sensor 19A. When only the right hand is in contact with the contact detection electrode pair, i.e. when SF is "2", control circuit 29 reads output Ce2 from alcohol sensor 19B. When both hands are in contact with the contact detection electrode pairs, i.e. when SF is "3", control circuit 29 reads both outputs Ce1 and Ce2.

Thereafter, control circuit 29 determines whether or not either output Ce1 or output Ce2 is equal to or larger than an alcohol drinking regulation value (S43). The alcohol drinking regulation value is set at a concentration of alcohol in perspiration vapor that corresponds to the concentration of alcohol in exhalation used to determine alcohol intoxication in regulation of drunk driving. For example, this value is specified as 0.15 mg per 1 L of exhalation according to Japan Road Traffic Law as of 2007. The alcohol drinking regulation value is predetermined as a value corresponding to the concentration used to determine alcohol intoxication, and stored in a memory of control circuit 29.

When neither output Ce1 nor output Ce2 is equal to or larger than the alcohol drinking regulation value (No in S43), control circuit 29 determines that the driver is not drunk. Then, the subroutine of FIG. 7 is terminated, and control is returned to the main routine. On the other hand, when either output Ce1 or output Ce2 is equal to or larger than the alcohol drinking regulation value (Yes in S43), control circuit 29 determines that the driver is drunk. In this case, control circuit 29 transmits a drinking alarm signal for the driver to the vehicle control circuit (S45). Upon receipt of the signal, the vehicle control circuit displays a warning to the driver in an indicator of the vehicle or the like.

Because continuing driving in the drunk condition is dangerous, control circuit 29 transmits a vehicle control signal to the vehicle control circuit (S47). Upon receipt of the vehicle control signal, the vehicle control circuit prompts the driver to stop the vehicle safely by forcing to decelerate the vehicle or controlling the vehicle so that the speed thereof is kept up to a predetermined value or lower. Alternatively, at the start of the vehicle, the start of the engine is inhibited. Thereafter, the subroutine of FIG. 7 is completed and control is returned to the main routine.

As described above, control circuit 29 determines that a palm is in contact with film 17, when at least one of resistance Rs1 between contact detection electrodes 21A and resistance Rs2 between contact detection electrodes 21B is within a predetermined range. When output Ce1 from alcohol sensor 19A or output Ce2 from alcohol sensor 19B with respect to the perspiration vapor sucked by pump 25 is equal to or larger than the alcohol drinking regulation value in this condition, control circuit 29 determines that the driver is drunk.

Though not shown in FIG. 7, it is preferable that control circuit 29 operates pump 25 at least when the vehicle is locked or unlocked. Then, output Ce1 from alcohol sensor 19A and output Ce2 from alcohol sensor 19B at that time are set as a value at which no alcohol is detected for calibration. With this setting, the zero point output from alcohol sensors 19A and 19B can be corrected every time when the vehicle is used. Thus, alcohol drinking conditions can be determined with high accuracy.

With the above structures and operations, control circuit 29 drives pump 25 only when control circuit 29 detects that a palm is in contact with film 17 covering opening 15, by the contact detection electrode pairs. This mechanism allows the perspiration from the palm to be positively evaporated and introduced into alcohol detection part 11, thus providing a high-accuracy drunk driving detection system capable of reducing the possibility of illicit acts and detecting alcohol concentrations in the perspiration vapor at a high speed.

In this exemplary embodiment, each of alcohol sensors 19A and 19B is made of thin-film semiconductor device 43 provided on micro heater 41. However, the present invention is not limited to this structure. For example, a catalytic-combustion alcohol sensor may be used. In such a type of sensor, a catalyst is provided on the micro heater and heated to a temperature appropriate for alcohol detection, and the temperature changes caused by alcohol combustion are detected. This type of alcohol sensor is small and has low power consumption, and thus is also preferable.

In this exemplary embodiment, two alcohol sensors 19A and 19B are used. However, as shown in FIG. 8, only one alcohol sensor 19 may be provided on the exhaust side of pump 25. In this case, only one alcohol sensor 19 does not have errors caused by variations in the output when a plurality of alcohol sensors 19 are provided, thus further improving the detection accuracy. However, in comparison with the structure including alcohol sensors 19A and 19B in alcohol detection parts 11, it takes more time for the perspiration vapor to reach alcohol sensor 19 in this structure, and thus requires a countermeasure, such as improvement of the suction capability of pump 25.

Further, in this structure, pump 25 sucks air from both openings 15, even when control circuit 29 detects contact in either one of contact detection electrodes 21A and 21B, i.e. when SF is "1" or "2". For this reason, similar to the second exemplary embodiment to be described later, correction to the output from alcohol sensor 19 is necessary in either of the case when SF is "1" or "2", and the case when SF is "3".

In this exemplary embodiment, alcohol detection parts 11 are provided in two positions in steering wheel 13. However, alcohol detection part 11 can be provided in at least one position. Disposing the alcohol detection part only in one position reduces the probability that a palm makes contact with film 17. This may raise the possibility that drunk driving cannot be determined adequately.

To address this problem, it is more preferable that a plurality of alcohol detection parts 11 (in 19 positions in FIG. 9), for example, are provided across steering wheel 13. Specifically, a plurality of openings 15 are provided in steering wheel 13, and partition walls 30 are provided between adjacent openings 15 inside of steering wheel 13. Then, alcohol sensor 19 is provided behind each of openings 15, and the suction side of pump 25 is connected to each of the openings 15. With this structure, even when a palm grasps any portion of steering wheel 13, the palm makes contact with one of films 17 and thus alcohol concentrations in perspiration vapor can be detected at all times. The structure of FIG. 9 includes 19 alcohol sensors. For the detection of an alcohol drinking condition, control circuit 29 can use the output only from alcohol sensors 19 behind openings 15 that have contact detection electrode pairs having a resistance within the predetermined range.

In the structure of FIG. 9, existence of a large number of alcohol sensors 19 can increase variations in output and decrease the accuracy in detecting an alcohol drinking condition. To determine an alcohol drinking condition with high accuracy, the drunk driving detection system may have a structure of FIG. 10. In this structure, pumps 25 are connected to openings 15 respectively and only one alcohol sensor 19 is provided in an integral part of pumps 25 on the exhaust side. FIG. 10 shows a structure including two openings 15 and two pumps 25, as an example. In this case, control circuit 29 operates only one of pumps 25 connected to opening 15 that includes a contact detection electrode pair having a resistance within the predetermined range. This mechanism prevents dilution of the perspiration vapor and thus allows detection of an alcohol drinking condition with high accuracy.

In this case, when one of pumps 25 is not driven, air is sucked only from opening 15 connected to the other one of pumps 25. Thus, the output from alcohol sensor 19 need not be corrected according to the SF value.

Second Exemplary Embodiment

Figure 11:
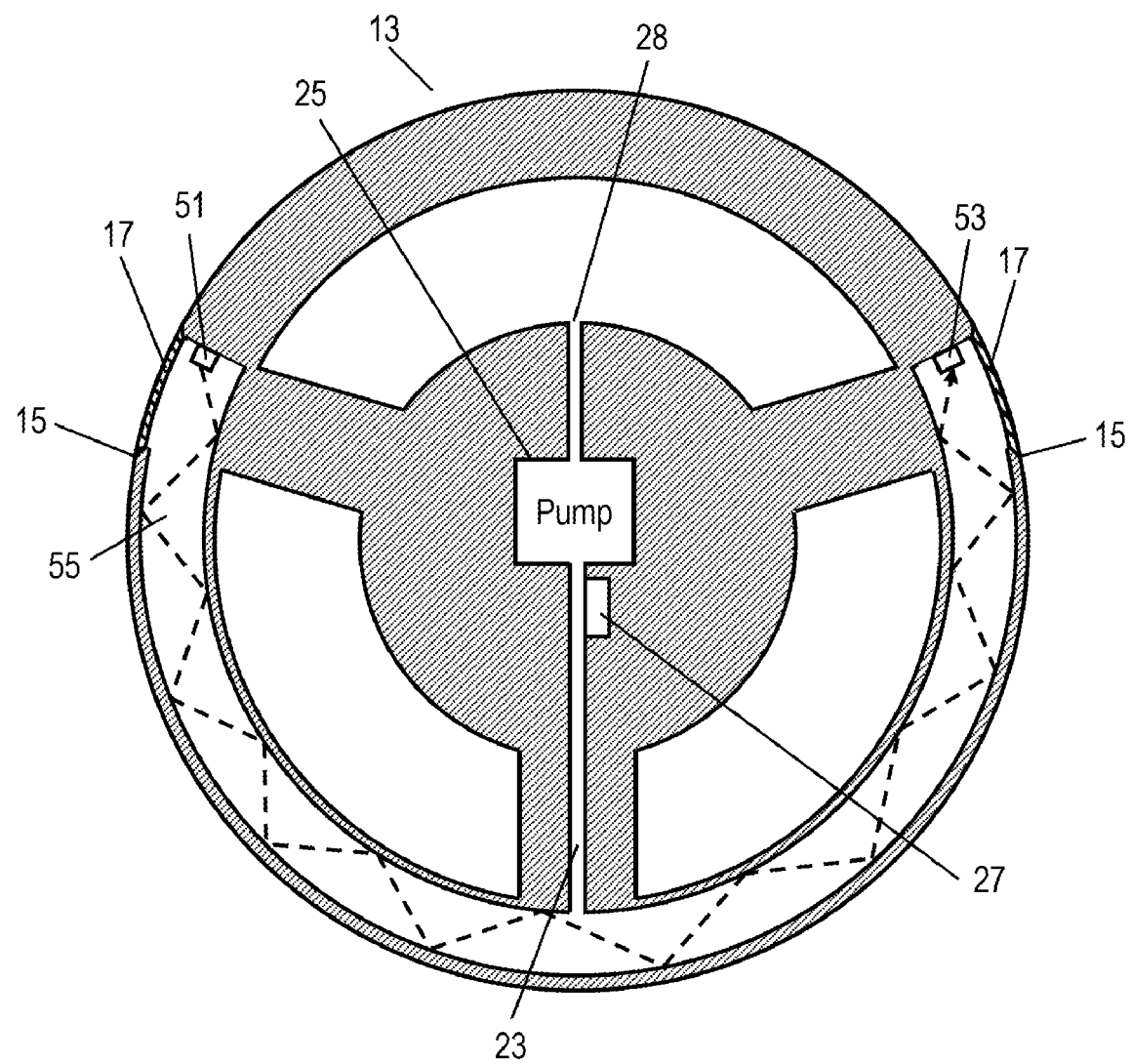
FIG. 11 is a schematic sectional view of a drunk driving detection system in accordance with a second exemplary embodiment of the present invention.
Figure 12:
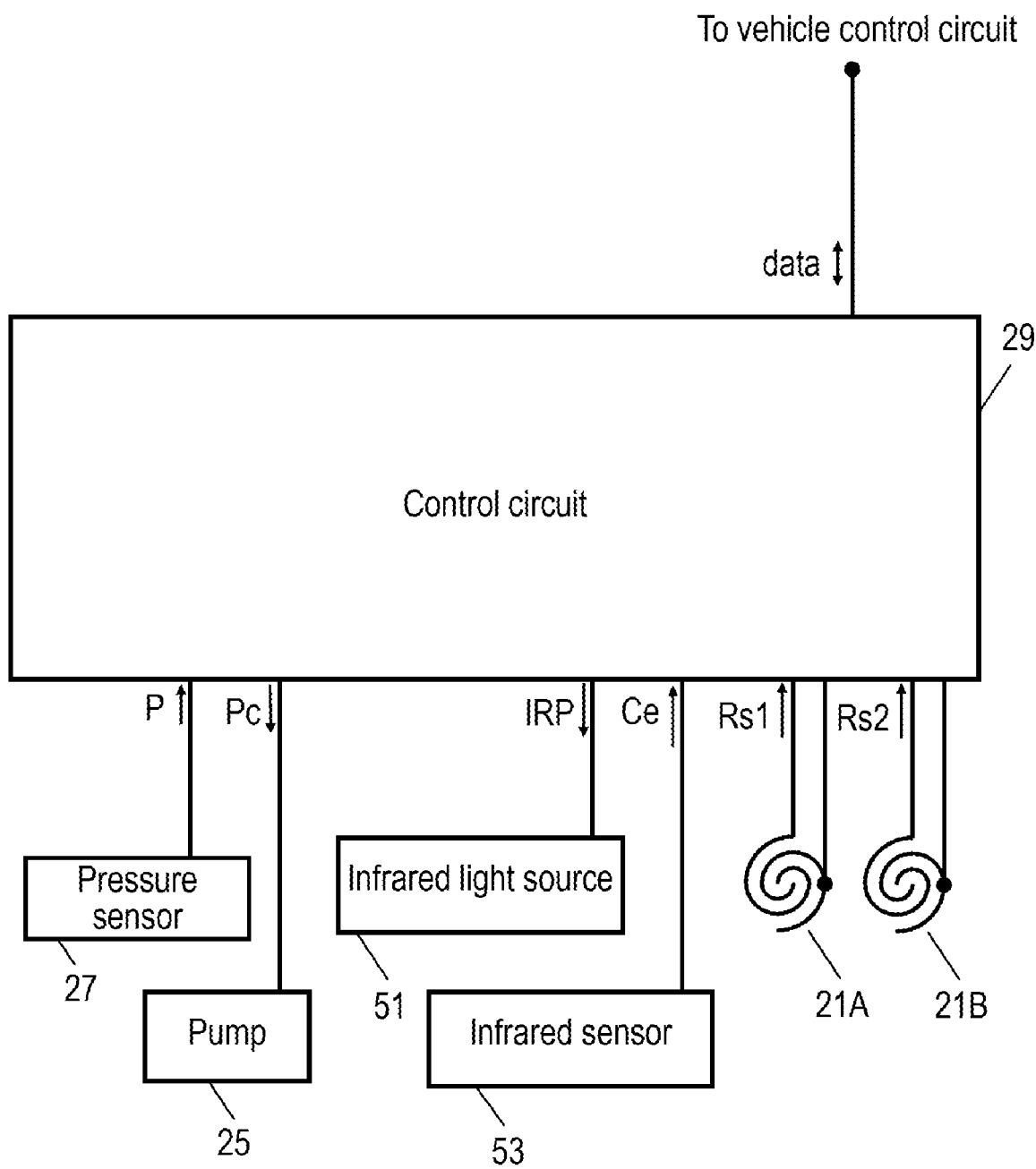
FIG. 12 is a block circuit diagram of the drunk driving detection system of FIG. 11.
Figure 13:
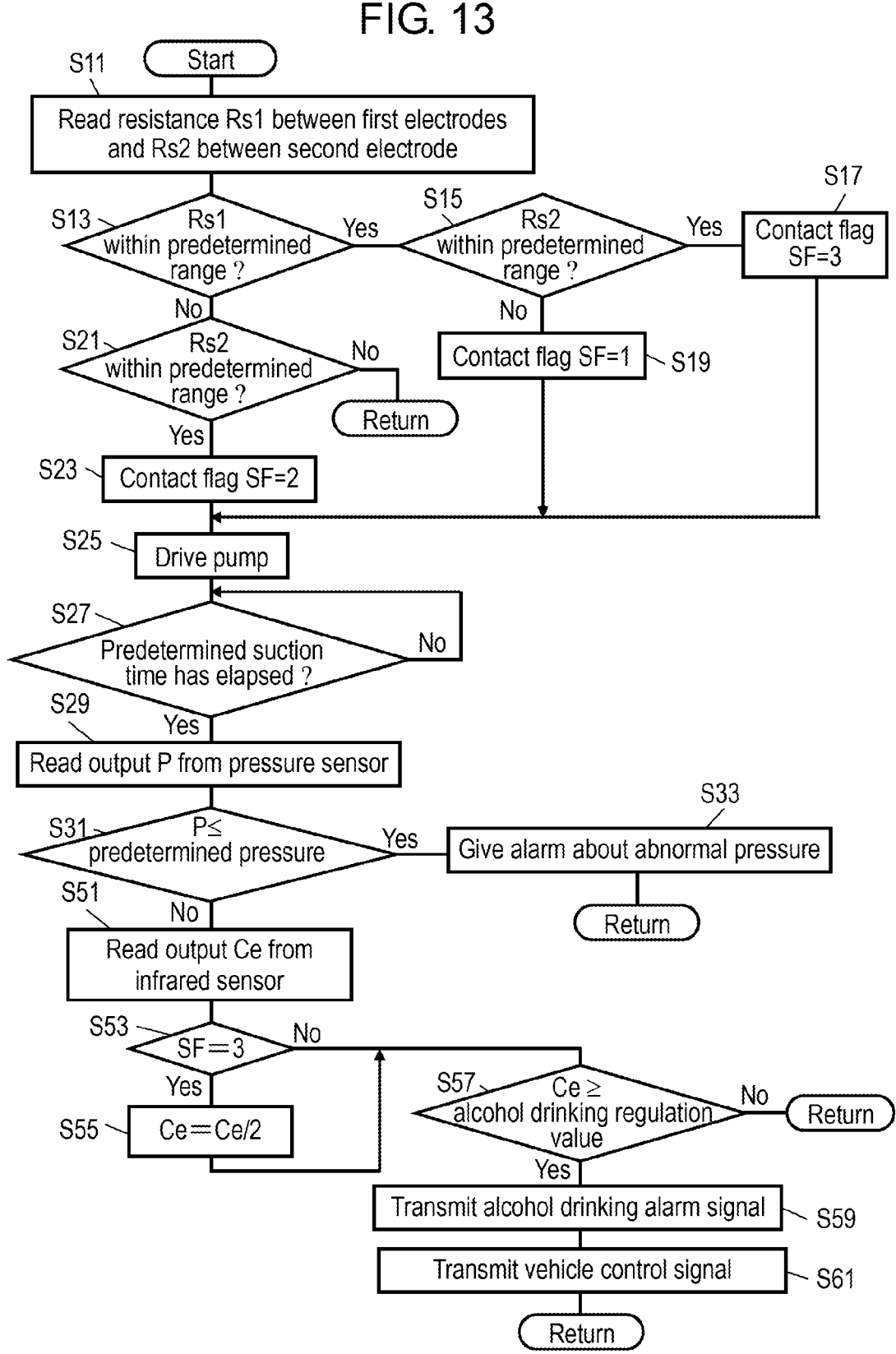
FIG. 13 is a flowchart showing the operation of the drunk driving detection system of FIG. 11.

FIG. 11 is a schematic sectional view of a drunk driving detection system in accordance with a second exemplary embodiment of the present invention. FIG. 12 is a block circuit diagram of the drunk driving detection system. FIG. 13 is a flowchart showing the operation of the drunk driving detection system. In the structure of the drunk driving detection system of the second embodiment, elements similar to those in the first embodiment have the same reference marks, and the detailed descriptions of those elements are omitted.

As shown in FIG. 11, the structure of this exemplary embodiment features that an alcohol sensor is formed of infrared light source (hereinafter "light source") 51 and infrared sensor (hereinafter "sensor") 53 both incorporated within steering wheel 13. Specifically, as shown by the dotted line in FIG. 11, an infrared ray generated from light source 51 repeatedly reflects in optical path 55 disposed along the circumferential direction of steering wheel 13 and reaches sensor 53. Light source 51 and sensor 53 are thus disposed. Further, openings 15 are provided through the surface of steering wheel 13 including optical path 55. Pump 25 is connected to optical path 55 by suction pipe 23. In this exemplary embodiment, as shown in FIG. 11, openings 15 are provided in two positions on the left and right sides in steering wheel 13. Light source 51 is disposed behind one of two openings 15 (on the left side in FIG. 11). Sensor 53 is disposed behind the other of openings 15 (on the right side in FIG. 11).

Next, a detailed description is provided of each of the featuring elements in this exemplary embodiment. Light source 51 may be formed of a heater. However, in this exemplary embodiment, a pyroelectric element is used as sensor 53. Thus, sensor 53 need be irradiated with pulse infrared rays. For this purpose, light source 51 is formed of a filament that generates pulse infrared rays according to on-off signals.

Sensor 53 is irradiated with pulse infrared rays as described above. However, when sensor 53 is irradiated with infrared rays having any infrared wavelength, detection of alcohol components is difficult. To address this problem, a filter (not shown) that selectively passes the infrared rays having wavelengths responsive to alcohol components is deposed above light source 51.

Infrared rays emitted from light source 51 through the filter are absorbed by alcohol components. Sensor 53 measures the intensity of the infrared rays that are not absorbed by the alcohol components and reach sensor 53. Control circuit 29 calculates the concentrations of the alcohol components based on the output from sensor 53.

Optical path 55 provided between light source 51 and sensor 53 is shaped like a cylinder formed in a part of the inside of steering wheel 13. The surface of optical path 55 is gold-plated so as to efficiently reflect the infrared rays. In this structure, as shown by the dotted line in FIG. 11, an infrared ray emitted from light source 51 repeatedly reflects on the surface of optical path 55 and reaches sensor 53. This structure increases the optical path length from light source 51 to sensor 53, and the output sensitivity of sensor 53, thus allowing detection of alcohol concentrations with high accuracy.

Formed on the surfaces of films 17 provided over two openings 15 are contact detection electrodes 21A and 21B having one of the configurations shown in FIG. 2A through 2C. Control circuit 29 operates pump 25 when at least one of a resistance between contact detection electrodes 21A and a resistance between contact detection electrodes 21B is within a predetermined range. With this structure, the perspiration vapor can positively be introduced across optical path 55, and infrared rays pass through the perspiration vapor. This structure allows alcohol components to be selected from the perspiration vapor and detected with high accuracy. The structure other than described above is similar to that of the first exemplary embodiment.

Next, a description is provided of a circuit structure of this exemplary embodiment, with reference to FIG. 12. In FIG. 12, elements similar to those in FIG. 3 have the same reference marks, and the detailed descriptions of those elements are omitted.

The structure of FIG. 12 features that light source 51 and sensor 53 are connected in place of alcohol sensors 19A and 19B of the first exemplary embodiment. In this structure, control circuit 29 supplies pulse drive current IRP to light source 51, and reads output Ce from sensor 53. The circuit structure other than described above is similar to that of the first exemplary embodiment.

Next, a description is provided of the operation in this exemplary embodiment, with reference to FIG. 13. In FIG. 13, the operations similar to those in FIG. 7 have the same step numbers, and the detailed descriptions of those steps are omitted.

In steps S11 through S33, the operations same as those in the first exemplary embodiment are performed. In the case of No in S31, control circuit 29 supplies pulse drive current IRP to light source 51 so that pulse infrared rays are generated for a predetermined period of time. Further, control circuit 29 reads output Ce from sensor 53 at that time (S51). Thereafter, control circuit 29 determines whether or not contact flag SF is "3" (S53). When SF is not "3" (No in S53), control is jumped to S57 to be described later. On the other hand, when SF is "3" (Yes in S53), both hands are in contact with two films 17, and the perspiration vapor from both hands is introduced into optical path 55.

At this time, when only one hand is in contact with one of films 17, air is introduced from opening 15 that is not in contact with the other hand. For this reason, the alcohol concentration in the perspiration vapor introduced is diluted to a half the actual alcohol concentration. In this exemplary embodiment, an alcohol drinking condition is determined on the basis of an alcohol concentration in the perspiration vapor from one hand, because the case of one hand has higher probability than the case where both hands are in contact with two films 17. Thus, when SF is "3", i.e. both hands are in contact with two films 17, an alcohol concentration twice the standard concentration is detected. Accordingly, control circuit 29 updates the Ce value by dividing output Ce from sensor 53 by two (S55).

Next, control circuit 29 compares output Ce from sensor 53 with an alcohol drinking regulation value (S57). The alcohol drinking regulation value is set to the same value as the first exemplary embodiment.

When output Ce is smaller than the alcohol drinking regulation value (No in S57), the driver is determined not to be drunk. Thus, the subroutine of FIG. 13 is terminated and control is returned to the main routine. On the other hand, when output Ce is equal to or larger than the alcohol drinking regulation value (Yes in S57), the driver is determined to be drunk. Then, similar to the first exemplary embodiment, control circuit 29 transmits a drinking alarm signal for the driver to the vehicle control circuit (S59). Control circuit 29 may also transmit a vehicle control signal to the vehicle control circuit (S61). Upon receipt of the signals, the vehicle control circuit gives an alarm to the driver and forcedly controls the vehicle. Thereafter, the subroutine of FIG. 13 is completed and control is returned to the main routine.

Also with such operations, an alcohol drinking condition of the driver can be determined. Further, unlike the structure of the first exemplary embodiment, the structure of this exemplary embodiment requires only one sensor 53 and one pump 25 for detection of alcohol concentrations, and does not require a plurality of alcohol sensors or pumps. Thus, a drunk driving detection system has a simplified structure. This drunk driving detection system is capable of improving detection accuracy without variations caused by a plurality of alcohol sensors and detecting alcohol drinking conditions at a higher speed, using infrared rays.

Similar to the first exemplary embodiment, it is preferable that pump 25 and light source 51 are operated when the vehicle is locked or unlocked, and output Ce from sensor 53 at that time is set as a value at which no alcohol is detected.

In this manner, pump 25 and light source 51 are driven only when contact of a palm with film 17 is detected in contact detection electrodes 21A or 21B. This operation allows the perspiration from the palm to be positively evaporated and introduced to alcohol detection part 11, while reducing the possibility of illicit acts. Further, the higher responsibility of sensor 53 allows detection of alcohol concentrations in the perspiration vapor at a higher speed. As power-consuming pump 25 and light source 51 are driven only when required, the power consumption can be reduced.

In the above description, openings 15 are provided in two positions on the left and right sides in steering wheel 13. The openings may be provided in any number of positions through the surface of steering wheel 13 including optical path 55. However, providing only one opening 15 reduces the probability that a palm makes contact with film 17. On the other hand, when a large number of openings 15 are provided, air is introduced also from openings 15 where film 17 is out of contact with a palm and dilutes the perspiration vapor. For these reasons, it is preferable that openings 15 are provided in two positions on the left and right sides in steering wheel 13.

In each of the first and second exemplary embodiments, control circuit 29 determines an alcohol drinking condition based on the alcohol concentrations in perspiration vapor. In addition to the alcohol concentrations, fatigue degrees of the driver may be used for determination. Specifically, line-of-sight detector 61 for detecting the lines of sight of the driver is provided in a place, e.g. the dashboard in front of the driver seat, and connected to control circuit 29, as shown in the block circuit diagram of FIG. 14. In this structure, control circuit 29 detects line-of-sight motion characteristics by line-of-sight detector 61, and calculates a fatigue degree of the driver based on the line-of-sight motion characteristics. When the fatigue degree is equal to or larger than a predetermined value and the output from the alcohol sensor is equal to or larger than the alcohol drinking regulation value, the driver is determined to be in a heavily drunk condition (first drunk condition). In this case, operations such as giving a stronger drinking alarm or forcedly stopping the vehicle may be performed. The fatigue degree can be obtained by calculating Lyapunov exponent λ expressed by Equation (1), for example:

$$\lambda = \lim_{n \to \infty} \frac{1}{n} \sum_{i=1}^{n} \ln\left|\frac{df(x_i)}{dx}\right| \quad (1)$$

Lyapunov exponent λ can be obtained as an extremal value when the line-of-sight motion characteristics are set as f(xi) in Equation (1), and modulus of variations (differential values) of the line-of-sight motion characteristics are averaged after logarithmic calculation. When the obtained Lyapunov exponent λ is equal to or larger than a predetermined value, control circuit 29 determines that the driver is tired.

Alternatively, weight sensor 62 may be provided in the driver seat in place of line-of-sight detector 61 so that control circuit 29 detects the weight change characteristics based on the output from weight sensor 62, and calculates the fatigue degree based on the weight change characteristics. Specifically, weight sensors 62 are provided in four corners of the driver seat, for example, and the displacement of the gravity center of the driver is obtained according to the weight change characteristics of each sensor. Calculation of Lyapunov exponent λ thereof can provide a fatigue degree. In such a structure, the driver seat weight sensor for a smart air-bag system can be used as weight sensor 62. Thus, in a vehicle incorporating a smart air-bag system, an alcohol drinking condition including a fatigue degree can be determined without the need of adding weight sensor 62.

Figure 14:
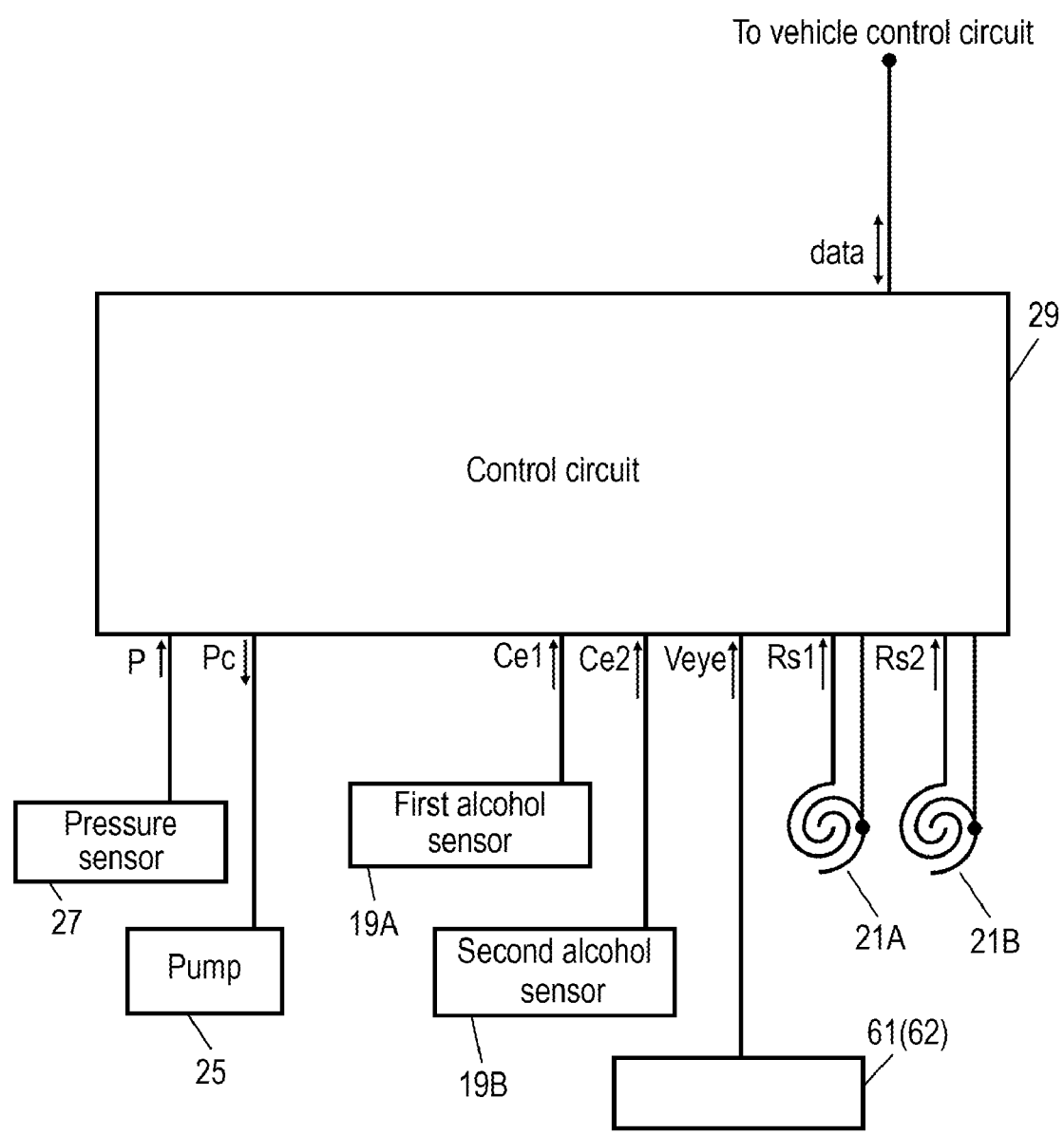
FIG. 14 is a block circuit diagram of another structure of the drunk driving detection system in accordance with the exemplary embodiments of the present invention.
Figure 15:
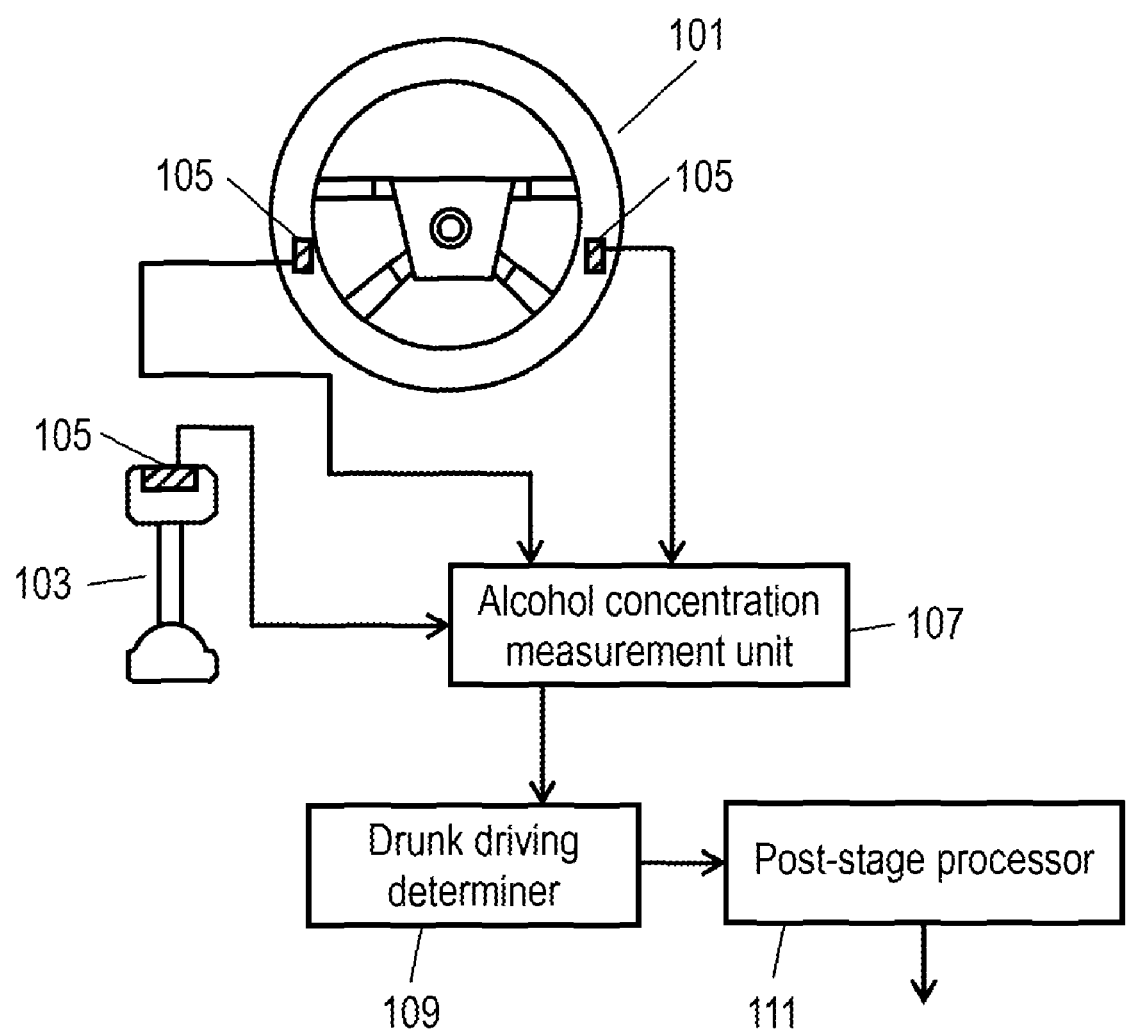
FIG. 15 is a schematic view showing a structure of a conventional drunk driving detection system.

When the fatigue degree obtained by line-of-sight detector 61 or weight sensor 62 described above is equal to or larger than a predetermined value, an alarm about fatigue may be given to the driver to prompt the driver to have a break, even though the diver is not in a drunk condition. Both line-of-sight detector 61 and weight sensor 62 may be provided. FIG. 14 shows a structure that includes line-of-sight detector 61 or weight sensor 62 added to the structure of FIG. 3. However, line-of-sight detector 61 or weight sensor 62 may be added to the structure of FIG. 12.

In each of the first and second exemplary embodiments, pump 25 sucks the perspiration vapor from opening 15 through film 17. However, pump 25 is not essential. In the first exemplary embodiment, for example, when alcohol sensors 19A and 19B are provided in contact with the edges around openings 15, and the responsibility of alcohol detection is ensured by the use of a material highly permeable to alcohol vapor or other methods, pump 25 can be eliminated.

In the above descriptions, the drunk driving detection system in each of the first and second exemplary embodiments is mainly for a motor vehicle. However, the drunk driving detection system may be used for the applications in which drunk operation gives serious influence, such as a railroad vehicle, an airplane, a marine vessel, construction equipment, and a plant actuator. Thus, the alcohol detection system as described above for a motor vehicle is just one example of particular application and the same can be applied to any other device or object which is controlled or monitored by a human.

The drunk driving detection system of the present invention can determine that the driver is in a drunk condition with high accuracy. Thus, the present invention is useful as a drunk driving detection system or the like particularly for private vehicles having a large number of drivers to which less strict control of drunk driving detection is given.

What is claimed is:

1. A drunk driving detection system for incorporation into a vehicle, the system comprising:
    a first liquid-impermeable and air-permeable film provided to cover a first opening in an object which is to be grasped by a driver of the vehicle;
    a pair of first contact detection electrodes provided on a surface of the first film;
    a first alcohol sensor provided to detect a level of alcohol introduced into the first opening; and
    a control circuit coupled to the first contact detection electrodes and the first alcohol sensor, the control circuit operable to measure a resistance between the first contact detection electrodes;
    wherein when the resistance is within a predetermined range, the control circuit determines the driver is in contact with the first film and detects an alcohol drinking condition of the driver based on an output from the first alcohol sensor.

2. The drunk driving detection system according to claim 1, further comprising:
    a pump coupled to the first opening on an intake side thereof, and electrically coupled to the control circuit;
    wherein when the control circuit determines the driver is in contact with the first film, the control circuit drives the pump and detects the alcohol drinking condition of the driver based on the output from the first alcohol sensor with respect to air sucked by the pump.

3. The drunk driving detection system according to claim 2, further comprising:
    a second liquid-impermeable and air-permeable film provided to cover a second opening in the object which is to be grasped by the driver of the vehicle;
    a second alcohol sensor provided to detect a level of alcohol introduced into the second opening;
    a pair of second contact detection electrodes provided on a surface of the second film, wherein:
    the intake side of the pump is coupled to the second opening; and
    the control circuit measures the resistance between the first contact detection electrodes and a resistance between the second contact detection electrodes, and detects an output from at least one of the first alcohol sensor or the second alcohol sensor corresponding to at least one of the first contact detection electrodes or the second contact detection electrodes that has the resistance therebetween within the predetermined range.

4. The drunk driving detection system according to claim 2, further comprising:
    a second liquid-impermeable and air-permeable film provided to cover a second opening in the object which is to be grasped by the driver of the vehicle;
    a pair of second contact detection electrodes provided on a surface of the second film; and
    a second pump is provided so that the second pump is coupled to the second opening on an intake side thereof, electrically coupled to the control circuit, and integral with the pump on an exhaust side thereof; wherein:
    the first alcohol sensor is provided in a portion in which the pump and the second pump are integral with each other on the exhaust side; and
    the control circuit measures the resistance between the first contact detection electrodes and a resistance between the second contact detection electrodes, and operates at least one of the pump or the second pump corresponding to at least one of the first contact detection electrodes or the second contact detection electrodes that has the resistance therebetween within the predetermined range.

5. The drunk driving detection system according to claim 2, wherein:
    the first alcohol sensor includes an infrared light source and an infrared sensor both incorporated within the object, and a hollow optical path is provided inside of the object;
    the infrared light source and the infrared sensor are disposed so that an infrared ray generated from the infrared light source reaches the infrared sensor along the optical path; and
    the first opening is disposed along the optical path, and the pump is coupled to the optical path.

6. The drunk driving detection system according to claim 5, wherein the object is provided with a second opening, the infrared light source is provided in proximity to the first opening, and the infrared sensor is provided in proximity to the second opening.

7. The drunk driving detection system according to claim 2, further comprising a pressure sensor coupled to the control circuit and located between the first opening and the pump;
    wherein the control circuit determines the first film is blocked when a pressure sensed by the pressure sensor during operation of the pump is equal to or lower than a predetermined value.

8. The drunk driving detection system according to claim 2, wherein the control circuit operates the pump at a time when the vehicle is locked or unlocked, and the output from the first alcohol sensor at the time the vehicle is locked or unlocked is set as a value at which no alcohol is detected.

9. The drunk driving detection system according to claim 1, wherein the first contact detection electrodes have a configuration in which the electrodes form an intricate pattern.

10. The drunk driving detection system according to claim 1, wherein the first alcohol sensor includes a micro heater, and a semiconductor device electrically insulated from the micro heater and provided above the micro heater.

11. The drunk driving detection system according to claim 10, wherein the control circuit detects an alcohol concentration by passing a pulse current through the micro heater.

12. The drunk driving detection system according to claim 11, wherein the control circuit passes a pulse current through the micro heater before detecting the alcohol concentration.

13. The drunk driving detection system according to claim 10, further comprising a plurality of the semiconductor device, and the first alcohol sensor includes the plural semiconductor devices.

14. The drunk driving detection system according to claim 13, wherein the control circuit sequentially switches the semiconductor devices every time when an alcohol concentration is detected.

15. The drunk driving detection system according to claim 1, wherein the control circuit sets the output from the first alcohol sensor as a value at which no alcohol is detected when the vehicle is locked or unlocked.

16. The drunk driving detection system according to claim 1, further comprising:
   at least one of a line-of-sight detector coupled to the control circuit for detecting a line of sight of the driver or a weight sensor coupled to the control circuit for sensing the weight of the driver;
   wherein, when the line-of-sight detector is provided, the control circuit detects line-of-sight motion characteristics by the line-of-sight detector, and calculates a fatigue degree of the driver based on the line-of-sight motion characteristics; and
   when the weight sensor is provided, the control circuit detects weight change characteristics by the weight sensor, and calculates a fatigue degree of the driver based on the weight change characteristics.

17. The drunk driving detection system according to claim 16, wherein when the fatigue degree is equal to or larger than a predetermined value and the output from the first alcohol sensor is equal to or larger than a predetermined alcohol drinking regulation value, the driver is determined to be in a first drunk condition.

18. The drunk driving detection system according to claim 16, wherein the control circuit obtains the fatigue degree by calculating a Lyapunov exponent.

19. An alcohol detection system for detecting an alcohol consumption level of a human, the system comprising:
   a liquid-impermeable and air-permeable film provided to cover an opening in an object which the human contacts;
   a pair of contact detection electrodes provided on a surface of the film;
   an alcohol sensor provided to detect a level of alcohol introduced into the opening; and
   a control circuit coupled to the contact detection electrodes and the alcohol sensor, the control circuit operable to measure a resistance between the contact detection electrodes;
   wherein when the resistance is within a predetermined range, the control circuit determines the human is in contact with the film and detects an alcohol consumption level of the human based on an output from the alcohol sensor.

20. The alcohol detection system according to claim 19, further comprising:
   a pump coupled to the opening on an intake side thereof, and electrically coupled to the control circuit;
   wherein when the control circuit determines the human is in contact with the film, the control circuit drives the pump and detects the alcohol consumption level of the driver based on the output from the alcohol sensor with respect to air sucked by the pump.

* * * * *